(12) United States Patent
List (10) Patent No.: US 7,976,479 B2
(45) Date of Patent: Jul. 12, 2011

(54) ANALYTICAL AID

(75) Inventor: Hans List, Hesseneck-Kailbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 368 days.

(21) Appl. No.: 11/859,753

(22) Filed: Sep. 22, 2007

(65) Prior Publication Data

US 2008/0065131 A1    Mar. 13, 2008

Related U.S. Application Data

(63) Continuation of application No. PCT/EP2009/060950, filed on Mar. 22, 2006.

(30) Foreign Application Priority Data

Mar. 24, 2005    (EP) .................................. 050006613

(51) Int. Cl.
*A61B 5/00*   (2006.01)
*A61B 17/14*  (2006.01)
*A61B 17/32*  (2006.01)
*B65D 81/00*  (2006.01)

(52) U.S. Cl. ........ 600/584; 600/573; 600/583; 606/181; 606/184

(58) Field of Classification Search .................. 600/583, 600/573; 606/181–183, 171
See application file for complete search history.

(56) References Cited

U.S. PATENT DOCUMENTS

| | | | | |
|---|---|---|---|---|
| 3,943,933 A * | 3/1976 | Gertzman | ..................... | 606/227 |
| 4,022,191 A * | 5/1977 | Jamshidi | ..................... | 600/566 |
| 4,442,836 A | 4/1984 | Meinecke et al. | | |
| 4,545,376 A | 10/1985 | Beiter | | |
| 4,648,408 A * | 3/1987 | Hutcheson et al. | ........... | 600/583 |
| 4,712,548 A * | 12/1987 | Enstrom | ..................... | 606/181 |
| 4,920,977 A * | 5/1990 | Haynes | ..................... | 600/583 |
| 5,019,047 A * | 5/1991 | Kriesel | ..................... | 604/132 |
| 5,047,044 A * | 9/1991 | Smith et al. | ..................... | 606/182 |
| 5,169,389 A * | 12/1992 | Kriesel | ..................... | 604/132 |
| 5,385,571 A * | 1/1995 | Morita | ..................... | 606/181 |
| 5,397,334 A * | 3/1995 | Schenk et al. | ................ | 606/182 |
| 5,411,480 A * | 5/1995 | Kriesel | ..................... | 604/133 |
| 5,454,828 A * | 10/1995 | Schraga | ..................... | 606/181 |
| 5,554,166 A | 9/1996 | Lange et al. | | |
| 5,741,288 A * | 4/1998 | Rife | ..................... | 606/181 |
| 6,464,649 B1 * | 10/2002 | Duchon et al. | ................ | 600/583 |

(Continued)

FOREIGN PATENT DOCUMENTS

DE    29 09 349    9/1980

(Continued)

*Primary Examiner* — Max Hindenburg
*Assistant Examiner* — Sean P Dougherty
(74) *Attorney, Agent, or Firm* — Bose McKinney & Evans LLP (57) ABSTRACT

An analytical aid including a base, a lancet and a test element. The lancet includes a lancet point and a distal end of the lancet can be attached to the base. At least the lancet point is located in a recess in the base and the recess can be closed by a cover as long as the analytical aid is in an unused state. The base includes a predetermined breaking point or position, at which the base is broken into two segments when stress is applied. The predetermined breaking point is arranged such that the lancet point is exposed for use when the base breaks at the predetermined breaking point. A test element is attached to the base.

29 Claims, 4 Drawing Sheets

U.S. PATENT DOCUMENTS

| | | | |
|---|---|---|---|
| 6,585,693 B1* | 7/2003 | Dischler | 604/171 |
| 6,875,223 B2* | 4/2005 | Argauer | 606/181 |
| 7,192,405 B2* | 3/2007 | DeNuzzio et al. | 600/583 |
| 7,223,248 B2* | 5/2007 | Erickson et al. | 600/584 |
| 7,291,117 B2* | 11/2007 | Boecker et al. | 600/583 |
| 7,343,188 B2* | 3/2008 | Sohrab | 600/345 |
| 7,655,017 B2* | 2/2010 | Starnes | 606/181 |
| 2002/0052618 A1* | 5/2002 | Haar et al. | 606/181 |
| 2002/0151920 A1* | 10/2002 | Marshall et al. | 606/181 |
| 2003/0050573 A1* | 3/2003 | Kuhr et al. | 600/567 |
| 2003/0212347 A1* | 11/2003 | Sohrab | 600/584 |
| 2004/0064068 A1* | 4/2004 | DeNuzzio et al. | 600/583 |
| 2005/0131440 A1* | 6/2005 | Starnes | 606/181 |
| 2005/0234368 A1* | 10/2005 | Wong et al. | 600/583 |
| 2005/0240207 A1* | 10/2005 | Marshall | 606/181 |
| 2005/0283094 A1* | 12/2005 | Thym et al. | 600/583 |
| 2006/0047294 A1* | 3/2006 | Mori | 606/181 |
| 2006/0129173 A1* | 6/2006 | Wilkinson | 606/181 |
| 2006/0174592 A1* | 8/2006 | Chan | 53/442 |
| 2006/0196031 A1 | 9/2006 | Hoenes et al. | |
| 2006/0241517 A1* | 10/2006 | Fowler et al. | 600/583 |
| 2006/0247555 A1* | 11/2006 | Harttig | 600/584 |
| 2007/0203514 A1* | 8/2007 | Flaherty et al. | 606/181 |

FOREIGN PATENT DOCUMENTS

| | | |
|---|---|---|
| DE | 101 42 232 | 3/2003 |
| DE | 103 15 544 | 10/2004 |
| EP | 0 088 257 | 9/1983 |
| EP | 0 656 970 | 5/1997 |
| EP | 1 508 304 | 10/2006 |
| WO | WO 98/48695 | 11/1998 |
| WO | WO 2004/066822 | 8/2004 |

* cited by examiner

Fig. 3B ically untrained people can carry out simple analyses of blood or interstitial fluid. In particular, where blood has to be obtained regularly, e.g., several times a day, by diabetics for monitoring blood-glucose concentration, lancets and accompanying devices (known as pricking aids) are available that make it possible for samples to be obtained as painlessly and reproducibly as possible. Such lancets and devices (pricking aids) are, for example, the subject of WO 98/48695, EP 0 656 970, U.S. Pat. No. 4,442,836 and U.S. Pat. No. 5,554,166.

ANALYTICAL AID

RELATED APPLICATIONS

This is a continuation application of International Application PCT/EP2006/060950, filed Mar. 22, 2006, which claims priority to EP 05006631.5, filed Mar. 24, 2005 which are hereby incorporated by reference in their entirety.

BACKGROUND

The present invention relates to an analytical aid comprising a lancet and a test element, an analyzer for the analysis of a sample by means of such an analytical aid, and a method for the analysis of a sample with the aid of such an analytical aid.

The examination of blood samples or interstitial fluid makes the early and reliable detection of pathological conditions and the targeted and verified monitoring of states of the body possible in clinical diagnostics. Medical diagnostics requires that a sample of blood or interstitial fluid is first obtained from the individual to be examined.

To obtain a sample, the skin can be perforated, for example at the finger tip or earlobe of the person to be examined, with the aid of a sterile, sharp lancet to obtain just a few microliters or less of blood for the analysis. This method is suitable, in particular, for the analysis of a sample that is carried out immediately or shortly after the sample is obtained.

In the area known as "home monitoring," medically untrained people can carry out simple analyses of blood or interstitial fluid. In particular, where blood has to be obtained regularly, e.g., several times a day, by diabetics for monitoring blood-glucose concentration, lancets and accompanying devices (known as pricking aids) are available that make it possible for samples to be obtained as painlessly and reproducibly as possible. Such lancets and devices (pricking aids) are, for example, the subject of WO 98/48695, EP 0 656 970, U.S. Pat. No. 4,442,836 and U.S. Pat. No. 5,554,166.

Self-determination of blood-sugar levels is today a globally widespread method of monitoring diabetes. Known blood sugar devices in the art comprise an analyzer into which a test element (test strip) is inserted. The test element is brought into contact with a drop of a sample, which has previously been obtained, for example, from the finger tip by a pricking aid.

The numerous system components (lancet, pricking aid, test element and analyzer) require considerable space and relatively complex handling. Systems also exist having a higher degree of integration, and consequently easier handling. For example, the test elements are stored in the analyzer and made available for measurement. A next step in miniaturization may be achieved, for example, through the integration of several functions or functional elements in a single analytical aid (disposable). For example, the operating sequence can be greatly simplified by suitable combination of the pricking procedure and sensor-based analyte concentration detection on one test element.

DE 103 15 544 relates to a method for producing combined pricking and measuring devices for detecting an analyte in a fluid, which include a support and a detection element. The method comprises the steps of forming recesses which define pricking points on one end face of the support material in strip form, applying a detection element to the support material in strip form and separating individual pricking/measuring disposable base bodies either individually or in groups from the support material at separating lines. The combined pricking and measuring devices can include individual pricking/measuring disposable base bodies which have a pricking point. The pricking point is provided with a soft plastic covering. The base body further includes a detection element, which after sterilizing and/or sealing of the individual pricking/measuring disposable base body, is applied to the latter.

DE 101 42 232 describes an analytical aid with a lancet and a test element. The lancet includes a lancet needle with a point and a lancet body, which completely surrounds the lancet needle, at least in the region of the point, the lancet needle being displaceable in relation to the lancet body. At least in the region of the point of the lancet needle, the lancet body consists of an elastic material, in which the point of the lancet needle is embedded. The analytical test element is fixedly connected to the lancet body.

One way of providing analytical aids encountered in the art is to provide the lancet with a capillary structure or to make it part of a capillary structure. Consequently, after pricking and the emergence of a drop of blood, the lancet point is moved to the blood in order to transport it with the capillary to test chemicals present on a test element. However, this can include several disadvantages.

The lancet point has to be kept sterile until immediately before use. Before use, the sterile protection has to be removed. After removal, it must not hinder the capillary function, but must be moved completely out of the blood path. The sterile protection may need to be removed, which can provide an individual part that is complicated to handle by a machine.

The capillary structure, which at least partially includes the lancet point, must be hydrophilic in order for the blood to be transported. However, up until the lancet is used, the sterile protection must provide a tight seal to prevent germs from getting in. Therefore, intimate contact between the sterile protection and the lancet point or the lancet stem is necessary. This intimate contact can, however, adversely change the surface properties, in particular, the hydrophilia of the lancet.

Once the blood has emerged, the opening of the capillary must directly contact the blood sample in order to be sucked up. There is a risk that the sharp point of the lancet will again prick the tissue. Therefore, exact knowledge of the position of the surface of the skin is required.

The production of analytical aids can include many problems. The lancet has to be sterilized and the sterility of the lancet has to be ensured throughout the time during which the analytical aid can be used. The test chemicals present in the testing area of the test element can be adversely influenced in the way in which they function and act by the known methods of sterilization. Sensitive chemicals or biological substances can be harmed. Therefore, the test chemicals should not be exposed to the sterilization process for the lancet.

SUMMARY OF THE INVENTION

Embodiments incorporating the present invention address the disadvantages of the prior art and the problems mentioned above.

One embodiment includes an analytical aid comprising a base body, a lancet and a test element, characterized in that i) the lancet has a proximal end and a distal end, the proximal end of the lancet being formed as a lancet point and the distal end of the lancet being fixedly connected to the base body, and at least the lancet point being embedded in a recess in the base body and the recess being closed by a covering when the analytical aid is in an unused state, and ii) the base body includes a predetermined breaking point or breaking position, at which the base body breaks up into two body parts or segments when stress is applied, the predetermined breaking point being arranged in such a way that the lancet point is exposed for use when the base body breaks up at the predetermined breaking point, and iii) the test element is fixedly connected to the base body.

In one embodiment of this analytical aid (or also called "disposable"), the three functions of pricking, sample taking and providing test chemicals for the analysis of a body fluid sample are combined.

The base body of the analytical aid serves as a support for the lancet and the test element and, before use, can be formed in one piece and advantageously in the form of a strip.

The lancet point can perforate the skin of a patient to obtain a blood sample or a sample of interstitial fluid. By embedding the lancet, in particular the lancet point, in the recess in the base body and by closing the recess with the covering, at least the lancet point can be kept sterile (germ-free) in the unused state until immediately before use. The two components of the analytical aid of the base body, the lancet and the test element can be prefabricated separately from one another. The sterilization can be performed (for example, by β or γ irradiation) before the test element is attached to the base body, so that the test chemicals are not exposed to the sterilization.

The base body can include a predetermined breaking point or location. The predetermined breaking point is designed such that the base body, which is designed to be brittle at least in the region of the predetermined breaking point, breaks up into two body parts or segments when a bending stress is applied at the predetermined breaking point. In this context, brittleness means in particular that the material has a small elongation at break. The material also has a low notched impact resistance. An advantageous material can include, for example, polymethyl methacrylate.

The position of the predetermined breaking point can be chosen such that the lancet point is exposed when the base body breaks up, in particular, such that the lancet point protrudes beyond the broken edge of the first body part.

The test element can be fixedly connected to the base body, advantageously by a known method, by adhesive bonding, welding, clipping or screwing. In this respect, the test element can be fixedly connected to the base body at two ends, in particular, the first end of the test element is connected to the first body part and the second end of the test element is connected to the second body part.

According to one embodiment, the recess in the base body is a longitudinal slit running in the longitudinal direction.

According to another embodiment, the lancet can include a knife-like blade (flat lancet), which tapers toward the lancet point. This knife-like blade is located in the recess in the base body, and generally is formed as a slit. When the base body breaks up at the predetermined breaking point, the knife-like blade of the lancet punches or cuts through the covering of the recess with its narrow (possibly sharpened) side, having an increased rigidity in the cutting direction on account of the width of the blade.

An embodiment of the invention includes a lancet having a first portion comprising the proximal end and a second portion connected to the distal end, the first portion being formed such that it is angled away from the second portion. The second portion of the lancet can be fixedly connected to the base body. In particular, the first portion can be arranged at an angle of about 90° in relation to the second portion. The first portion (for example in the form of a knife-like blade) can then come to lie in a recess in slit form, while the second portion, arranged perpendicular thereto, rests on the surface of the base body running perpendicular to the slit, and can be fixedly connected to it.

The covering can include at least one film, which entirely or partially covers at least one surface of the base body. The films can be as thin as possible. They can be provided on the upper side and the underside of the base body. The material of the films are preferred to be as compatible as possible with the material of the base body, for example, being welded with the base body. For the analytical aid to be used, it is preferred that it readily tear in a region intended for this. A break in the base body may in this case serve as a notch that initiates tearing of the film. Materials of the covering can include, for example, polystyrene or cellophane. Generally, the films have a thickness of between 2 and 20 µm, and advantageously have thicknesses between 5 and 15 µm.

The covering can, for example, be connected to the base body by adhesive, bonding or welding. In particular, in the region of the predetermined breaking point, the covering can be attached to the base body of the analytical aid such that, when the base body breaks up into two body parts, the covering is likewise severed and does not become prematurely detached from the base body.

The material of the base body (in particular, in the region of the predetermined breaking point) can be formed from plastic.

According to one embodiment, the base body and/or the covering consist of a material that can be made brittle by irradiation. For example, the base body can be a plastic support and the covering a number of films that become highly brittle by exposure to γ radiation. This allows production of the base body and/or the covering from a roller on which the basic components of the base body and the covering can be wound up due to their original flexibility. After production, the embrittlement of the base body and/or the covering takes place by the irradiation, so that when the analytical aids produced in this way are used, breaking up of the base body and/or the covering can be ensured. A possible material for this variant is polystyrene.

According to a further embodiment, the base body of the analytical aid can be produced as an (in particular, symmetrical) injection-molded part.

The predetermined breaking point of the base body can preferably take the form of lateral notches and/or at least one transverse channel in the base body.

According to another embodiment, the test element can be made at least partially of a flexible material. In this context, flexible can mean that the material of the test element is adequately deformable to allow it to be wound up on a roller before the production of the analytical aid, to allow it before use to be fastened in the form of at least one loop to the base body, and to allow it during use to be stretched over a component of the analyzer in which the analytical aid is used, so that the test element comes into close contact with the surface of the component. The test element can be, for example, a portion of a flexible test strip, which includes a testing area. The test element can be fixedly connected to the base body at two ends.

One embodiment is designed such that, before the analytical aid is used, the test element has at least one loop, which can be detachably connected to the base body or the covering. Advantageously, before use, the test element fastened to the base body includes two loops, which are only, i.e., in the unused position of the analytical aid, attached on both sides next to the testing area. Consequently, before use of the analytical aid, the test element can be collapsed in a space-saving manner and does not flap. For use, it can then be detached from the base body at the detachable locations and folded to its full length.

Another embodiment includes an analyzer for the analysis of a sample by an analytical aid. The analyzer can include two holding elements for receiving the two body parts of the broken-up base body of the analytical aid and a measuring head, over which the at least partially flexible test element can be stretched. The measuring head can include the form of a finger (for example, in the tip of the finger) and contains a measuring arrangement for the analysis of a sample that is located on the testing area of a test element lying against the measuring head. For the analysis of the sample, optical methods (such as reflection photometry, absorption measurement or fluorescence measurement) or electrochemical methods (such as potentiometry, amperometry, voltametry or coulometry) can be used.

The holding elements and the measuring head can be displaceable parallel to one another. This can enable the holding element, which fixes the body part that is connected to the lancet, to be displaced in such a way that the lancet point performs a pricking movement. In this case, the other body part can be displaced with the other holding element in the opposite direction, in order to maintain a certain tension of the test element stretched over the measuring head. After pricking the skin of a user with the lancet point to produce a perforation, the measuring head (for example in finger form) can be displaced in the direction of the perforation to be able to receive a sample (blood or interstitial fluid).

According to another embodiment, the analyzer includes a bending device for breaking up the base body of the analytical aid before use into the two body parts by applying a bending force to the base body. For example, the bending device can be a closure of the analyzer which, after insertion of an analytical aid into one of the holding elements, is swung closed. The bending device thereby interacts with the measuring head in such a way that the base body is bent over the measuring head until it breaks up at the predetermined breaking point into the two body parts.

One embodiment relates furthermore to a method for the analysis of a sample with the aid of an analytical aid including the steps of A) inserting one end of the analytical aid into a first holding element in an analyzer, B) breaking the base body of the analytical aid into a first body part and a second body part and opening the covering, the lancet point being exposed for use by remaining fixedly connected to the first body part and protruding beyond it, C) stretching the at least partially flexibly formed test element, which is fastened to both body parts, over a measuring head contained in the analyzer, the first body part being fixed in the first holding element and the second body part being fixed in a second holding element in the analyzer, D) taking the sample by pricking with the lancet point at a sample-taking location and receiving the sample on the test element stretched over the measuring head, so that the sample is transferred to a testing area of the test element, and E) analyzing the sample present in the testing area by the measuring head.

The insertion of the analytical aid in step A) of the method can be performed automatically or manually. The insertion can be performed, for example, by fitting one end of the base body into a first holding element having a corresponding depression.

The breaking of the analytical aid according to step B) can be performed by applying a bending force to the base body of the analytical aid, so that it breaks up at the predetermined breaking point into the two body parts. The covering can be thereby broken up, either by breaking up on account of the bending force or by being cut open by the lancet, which protrudes beyond the broken edge of the first body part and does not break up. The bending force may be applied, for example, by a bending device of the analyzer or manually.

The stretching of the test element in step C) can have the effect that any loops of the test element are undone and the testing area present on the test element is brought into a measuring position or into the vicinity of a measuring position. Therefore, the at least one loop of the test element can be detached from the body parts during the stretching of the test element in step C).

The pricking of a sample-taking location (for example, the skin of the finger tip) by the lancet point in step D) can be performed by an automatic advancing and retracting movement of the lancet point through an opening in the housing of the analyzer. Subsequently, the measuring head with the test element stretched over it can be likewise moved through the opening in the housing of the analyzer and brought into an exposed position, in which the sample can be transferred to a receiving location on the test element that either lies directly on or at the testing area or is designed such that transporting of the sample to the testing area is ensured (for example through a capillary). Therefore, the measuring head with the test element stretched over it and the body parts can be displaced with respect to one another, in order in step D) first to move the lancet to the sample-taking location and then to bring the measuring head into position for receiving the sample.

The analysis of the sample in step E) can be carried out by one of the aforementioned optical or electrochemical methods of analysis, the testing area of the test element being located in a measuring position.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present embodiments.

Figures 1A, 1B:
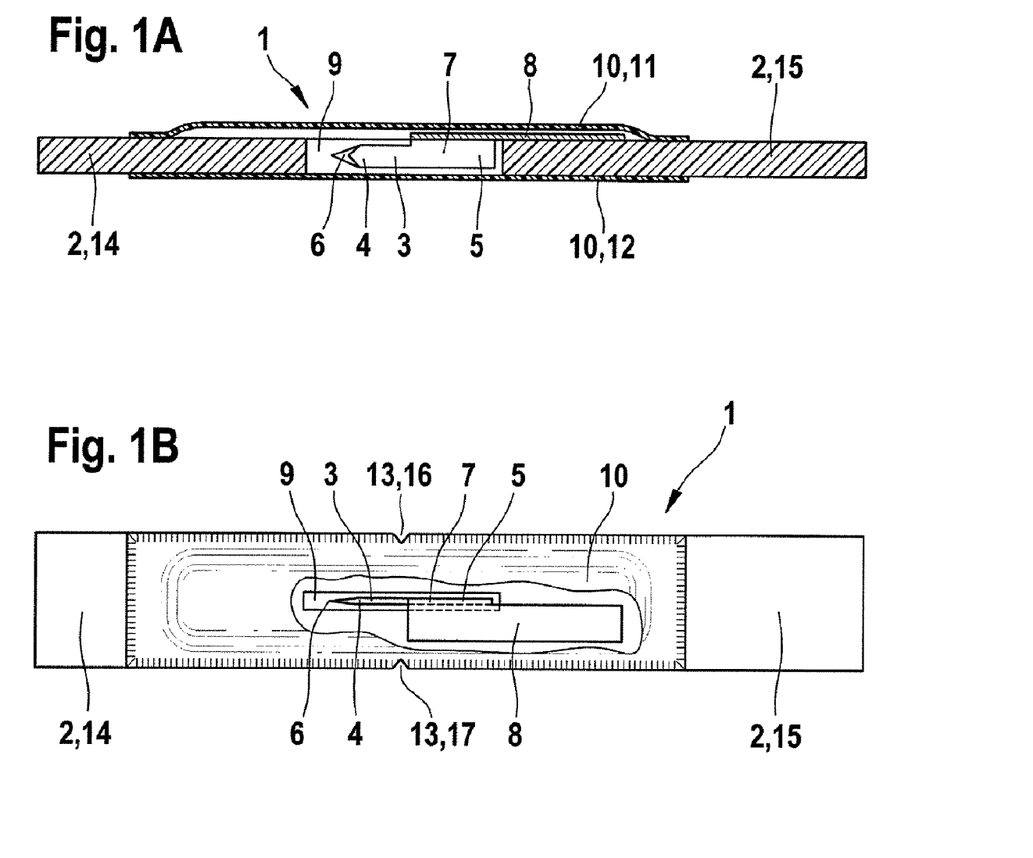
FIG. 1A is a side sectional view of a base body and a lancet fastened to it of an analytical aid.
FIG. 1B is a top view with interior portions exposed of a base body and a lancet fastened to it of an analytical aid.

FIGS. 1A and 1B show a sectional representation of a base or base body and a lancet fastened to it of an analytical aid from the side and from above, respectively. The analytical aid 1 comprises a base body 2 and a lancet 3. The base body 2 is, for example, a plastic support. In addition, the analytical aid comprises a test element (not shown in FIGS. 1A and 1B).

The lancet 3 includes a proximal end 4 and a distal end 5. The proximal end 4 can be formed as a lancet point 6. The distal end 5 can be attached or fixedly connected to the base body 2. The lancet 3 includes a first portion 7 having the proximal end 4 and a second portion 8 connected to the distal end 5. The first portion 7 can be arranged at an angle of about 90° in relation to the second portion 8. This can be seen in particular in FIG. 1C. The second portion 8 can be fixedly connected to the base body 2. This connection can be created in the production of the analytical aid 1, for example, by adhesive bonding, welding, clipping or screwing. In the case of the analytical aid 1 according to FIG. 1A, the first portion 7 (including the lancet point 6) of the lancet 3 can be embedded in a recess 9 in the base body. The recess 9 can be a slit, which is arranged centrally and in the longitudinal direction in the base body 2. The recess 9 extends from top to bottom and serves for receiving the sharpened part of the lancet 3 as long as the analytical aid 1 is positioned in the unused position, i.e., is being stored and not yet being used. The recess 9 can be closed on both sides by a covering 10. This covering 10 includes two thin films 11, 12, with which the upper side and underside of the base body 2 are sealed. By this covering 10, it is ensured that the previously sterilized lancet point 6 can be kept sterile in the closed recess 9 until shortly before the analytical aid 1 is used.

The base body 2 also includes a predetermined breaking point or position 13, at which the base body 2 breaks up into two part-bodies (body parts) 14, 15 when stress is applied (in particular, a bending stress). The predetermined breaking point 13 can be defined by lateral notches 16, 17 in the base body 2. When a bending stress is applied to the base body 2, it can break along a line, which runs from one notch 16 to the other notch 17, into two body parts 14, 15, without damaging the lancet 3. The predetermined breaking point or location 13 is in this case arranged in such a way that the lancet point 6 is exposed for use when the base body 2 breaks into the two body parts 14, 15. This takes place by cutting up or tearing of the covering 10 so that the lancet point 6 protrudes beyond the broken edge of the second body part 15.

In the region of the predetermined breaking point 13, the covering 10 is intimately connected to the base body 2. Both the covering 10 and the base 2 advantageously consist of a material that becomes highly brittle by exposure to γ radiation. This allows production from a roller and nevertheless simplifies the breaking apart of the base body 2 together with the films serving as the covering 10 possible when the analytical aid 1 is used.

Figure 1C:
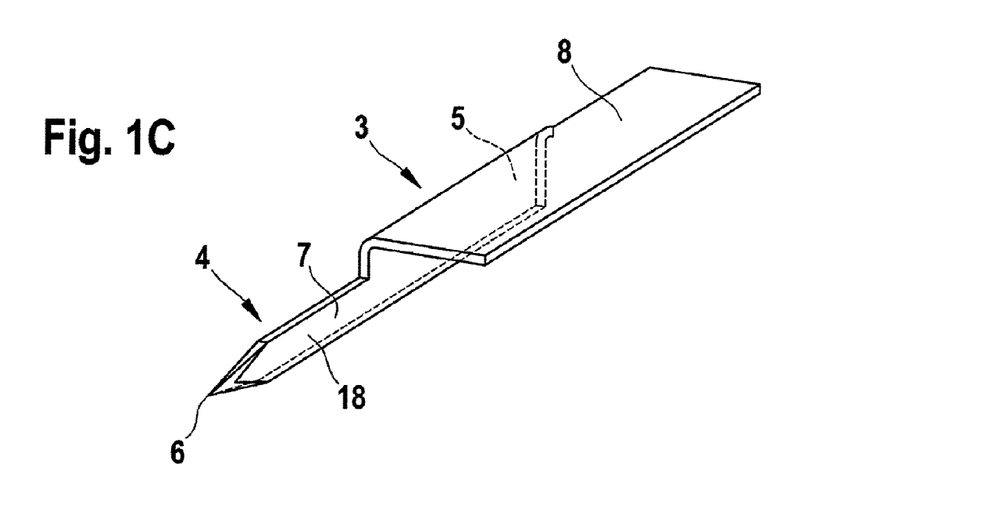
FIG. 1C is a perspective view of a lancet for an analytical aid.

FIG. 1C shows a lancet for an analytical aid, as used in the analytical aid according to FIGS. 1A and 1B. The lancet 3 comprises two portions 7, 8, which can be arranged at an angle of 90° in relation to each other. The first portion 7 comprises a knife-like blade 18 (flat lancet), which tapers toward the lancet point 6. When the base body 2 surrounding the first portion 7 of the lancet 3 in the analytical aid 1 breaks up, the blade 18 can cut through the films serving as the covering 10. The second portion 8 of the lancet serves for fastening it to the base body 2 of an analytical aid 1.

Figure 2:
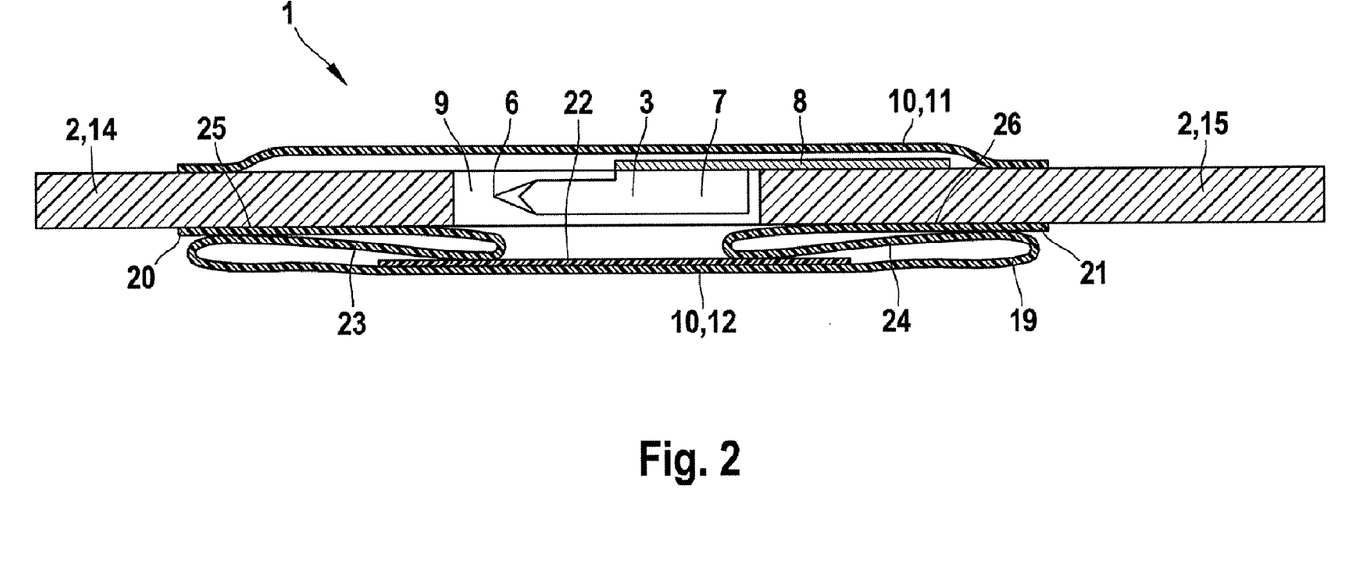
FIG. 2 is a side sectional view of an analytical aid.
Figure 3A:
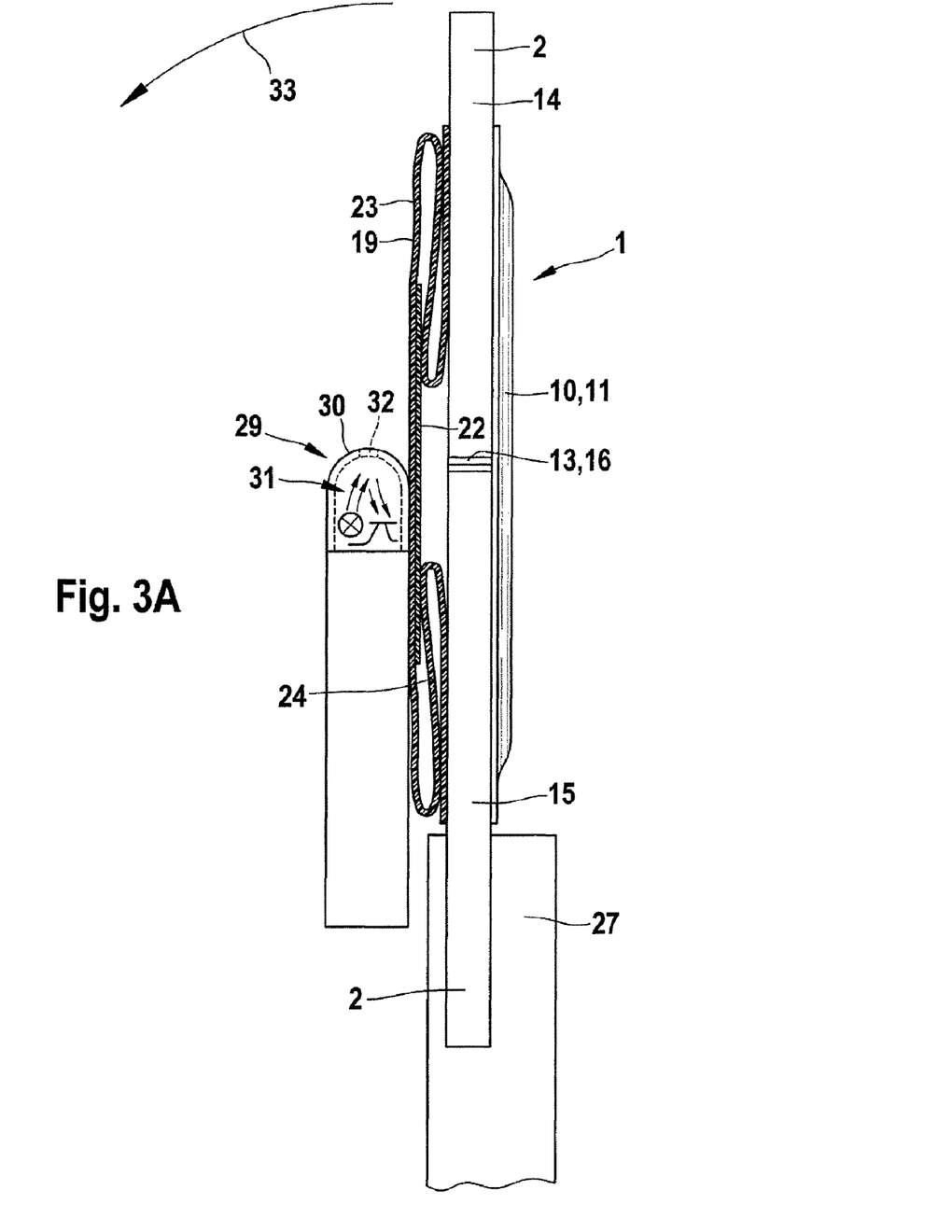
FIG. 3A is a schematic representation of a detail of an analyzer, with an inserted analytical aid.
Figure 3B:
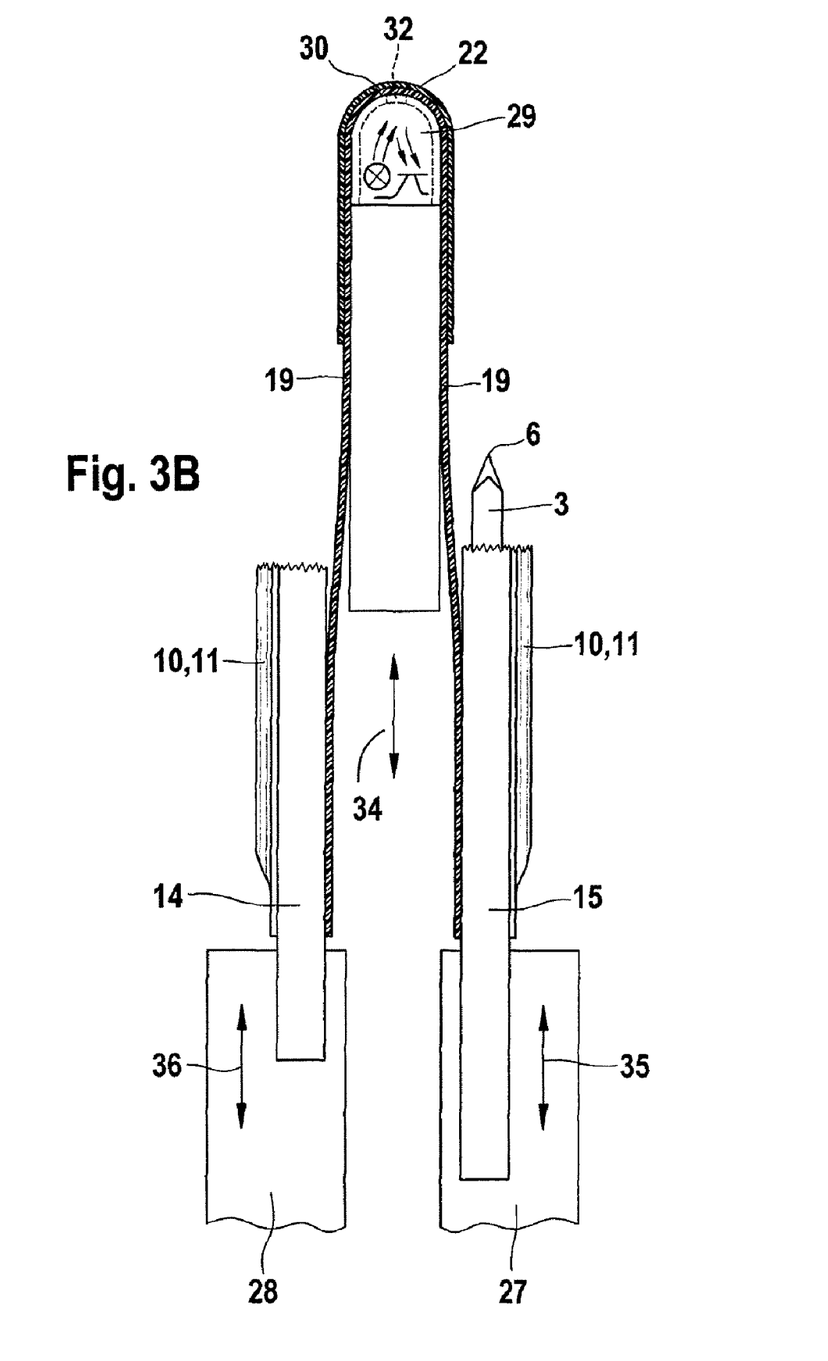
FIG. 3B is a schematic view showing the detail from FIG. 3A, the base body of the analytical aid being broken up into two body parts or segments and the test element being stretched over a measuring head.

FIG. 2 shows a sectional representation of an analytical aid from a side. The construction of the analytical aid 1 represented in FIG. 2 corresponds to that already described with respect to FIGS. 1A to 1C. In addition, a test element 19 is represented in FIGS. 3A and 3B. The test element 19 can be attached or fixedly connected to the base body 2 at two ends 20, 21. The test element 19 includes a flexible material and a testing area 22 with testing chemicals. The testing area 22 is facing the base body 2. In this analytical aid 1, it is intended for the sample (for example, blood) to be applied directly to the testing area 22. The testing area 22 therefore corresponds to the application area for applying the sample to be analyzed.

The test element can be produced from a flexible test strip. A portion of such a flexible test strip includes a testing area 22. The test element 19 includes two loops 23, 24, which can be detachably connected to the base body at the connecting locations 25, 26. In the production of the test element 19 from a portion of test strip, the latter is folded and fastened to the base body 2 (or the covering 10) in such a way that the ends of the portion of strip are fixedly connected to the analytical aid 1 (for example, by adhesive bonding). The two long pieces of the portion of strip that are made into loops 23, 24 are only lightly attached to the left and right of the testing area 22, so that they are prevented from flapping and can be easily detached.

The component shown in FIGS. 1A-1C of the analytical aid according to FIG. 2 (base body 2, lancet 3, covering 10) can be produced separately from the test element 19, so that the test chemicals of the testing area 22 are not adversely influenced by the sterilization of the lancet 3.

FIG. 3A shows a schematic representation of a detail of an analyzer with an inserted analytical aid. The detail shown is located within a housing (not represented) of the analyzer and is therefore not visible to a user from the outside. The analyzer serves for the analysis of a sample of an analytical aid by an optical method of analysis. The analyzer includes two holding elements 27, 28 for receiving the two body parts 14, 15 of the base body 2 of an analytical aid 1. Furthermore, the analyzer includes a measuring head 29, over which the remaining test element 19 can be stretched and which is arranged between the two holding elements 27, 28 (element 28 shown in FIG. 3B) during the perforation of the skin of a user by the lancet 3 and during the sample taking.

FIG. 3A shows the analytical aid 1, which has been inserted by a user with one end into the first holding element 27 of the analyzer. The first holding element 27 is a kind of clasp, which encloses the end of the analytical aid 1 and thereby fixes it. The measuring head 29, in finger form in this case, can be arranged parallel to the analytical aid 1. In this position, its rounded-off end 30 can be located at the level of the predetermined breaking point 13 of the base body 2. In the rounded-off end 30 of the measuring head 29 there are measuring optics 31 (for example, in the form of a light-emitting diode and a photodiode), which can interact with the outside (in particular, with an analyte on a testing area) via a transparent window 32 in the tip of the measuring head 29.

The base body of the analytical aid 1 can be bent in the direction of the arrow 33 over the rounded-off end 30 of the measuring head 29 until it breaks up at the predetermined breaking point 13 into the two body parts 14, 15. The covering 10 (films) is thereby opened, either by breaking up due to the bending stress or by being cut up by the lancet 3. As a result, the lancet point 6 can be exposed for use. It protrudes beyond the broken edge of the second body part 15 and remains connected to it (see FIG. 3B). The bending deflection for breaking up the base body 2 takes place by a bending device (not represented) that is contained in the analyzer. This may be, for example, a flap of the analyzer, which the user manually closes after insertion of the analytical aid 1 into the analyzer and which exerts a force in the direction of the arrow 33 on the base body 2 when it closes. At the same time, the end of the base body 2 that is facing away from the first holding element 27 slides into a second holding element 28 (not represented in FIG. 3A), which is formed like the first holding element 27 and fixes the first body part 14 after the breaking up of the base body 2.

FIG. 3B shows the detail of the analyzer from FIG. 3A, the base body of the analytical aid having broken up into two body parts and the test element having been stretched over the measuring head.

The two body parts 14, 15 can be respectively fixed by holding elements 27, 28. The test element 19, shown collapsed in FIG. 3A, can be stretched over the measuring head 29. The measuring head 29 can be formed resiliently in direction 34, in order that a basic tension of the test element 19 bent over the measuring head 29 can be always maintained. When the test element 19 is stretched over the measuring head 29, the two loops 23, 24 are detached from the body parts 14, 15 and the test element 19 unfolds to its full length. The holding elements 27, 28 and the measuring head 29 are displaceable parallel to one another. As a result, first the lancet 3 can be moved to the sample-taking location and then the measuring head 29 can be brought into position for receiving the sample. The holding elements 27, 28 are displaced in phase opposition to each other by a drive (not represented) in the directions 35, 36 (like a rocker), so that the test element 19 thereby remains stretched.

For the taking of a sample, the first holding element 27 is displaced (upward in FIG. 3B), so that the lancet point briefly emerges through an opening (not represented) in the housing of the analyzer and perforates the skin of a user at a sample-taking location, for example, the skin of a finger tip placed there. Then, the first holding element 27 with the body part 15 fixed to it and the lancet 3 can be retracted again completely into the housing of the analyzer. The second holding element 28 with the first body part 14 performs a movement opposed to the movement of the first holding element 27, in order that the test element 19 remains stretched over the measuring head 29. Subsequently, the measuring head 29 (and consequently also the holding elements 27, 28 with the component parts of the analytical aid 1) can perform a lateral movement or pivoting movement, so that the measuring head 29 can be pushed through the opening in the housing of the analyzer to the taking location. This may take place, for example, by displacing the measuring head 29 together with the holding elements 27, 28 and the component parts of the analytical aid 1 or the measuring head 29 alone toward the opening (upward in FIG. 3B). As soon as the measuring head 29 protrudes from the housing of the analyzer through the opening, the sample (blood or interstitial fluid) can be transferred to the test element 19 stretched over the measuring head 29, so that it is passed to a testing area 22 of the test element 19. The sample is thereby advantageously transferred directly to the testing area 22 arranged on the rounded-off end 30 of the measuring head 29. In this case, no capillary gap is required for transporting the sample to the testing area, so that problems with hydrophilia or surface tension are reduced or eliminated. Furthermore, two-dimensional dosing is concerned in this case, which makes the receiving of the sample less sensitive to tolerances. Furthermore, there is the possibility of using a low force to make the testing area 22 move against the surface of the skin at the sample-taking location, in order to ensure that the sample is taken over onto the testing area 22. Renewed pricking of the skin with the lancet point 6 can be advantageously avoided with the analyzer.

The sample present on the testing area 22 is subsequently analyzed by the measuring optics 31 in the measuring head 29.

While exemplary embodiments incorporating the principles of the present invention have been disclosed herein-above, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMERALS 1 analytical aid
2 base body
3 lancet
4 proximal end of the lancet
5 distal end of the lancet
6 lancet point
7 first portion of the lancet
8 second portion of the lancet
9 recess
10 covering
11 first film
12 second film
13 predetermined breaking point
14 first body part
15 second body part
16 first lateral notch
17 second lateral notch
18 knife-like blade
19 test element
20 first end of the test element
21 second end of the test element
22 testing area
23 first loop of the test element
24 second loop of the test element
25 first connecting location
26 second connecting location
27 first holding element
28 second holding element
29 measuring head
30 rounded-off end of the measuring head
31 measuring optics
32 window
33 direction of arrow
34 direction of displacement of the measuring head
35 direction of displacement of the first holding element
36 direction of displacement of the second holding element

What is claimed is:

1. An analytical aid for analyzing a body fluid, comprising:
a base that is breakable into a first segment and a second segment to produce a broken edge when a bending force is applied to the base, the base having a recess;
a lancet connected to the base and having a lancet point that is located in the recess when the analytical aid is in an unused state, the lancet point becoming exposed for puncturing a body part when the base is broken into the first segment and the second segment;
a test element at which a body fluid is analyzed attached to the base; and
a cover that covers the lancet point when the analytical aid is in the unused state, wherein the lancet ruptures the cover when the base is broken and the analytical aid is moved from the unused state.

2. The analytical aid of claim 1, wherein the recess includes a slit running substantially along a longitudinal direction of the analytical aid.

3. The analytical aid of claim 1, wherein the lancet comprises a first portion that is connected to the base and a second portion that includes the lancet point, the first and second portions being angled relative to one another.

4. The analytical aid of claim 1, wherein at least one of the base and the cover comprises a material made brittle by irradiation.

5. The analytical aid of claim 1, wherein the lancet point ruptures the cover when the base is broken and the analytical aid is moved from the unused state.

6. The analytical aid of claim 1, wherein the base comprises a predetermined breaking position comprising at least one of a notch and a channel formed in the base.

7. The analytical aid of claim 1, wherein the test element includes an application area for applying a sample to be analyzed, the application area facing the base when the analytical aid is in the unused state.

8. The analytical aid of claim 1, further comprising a measuring head, wherein the test element is at least partially flexible and is stretchable over the measuring head during use of the analytical aid.

9. The analytical aid of claim 8, wherein the test element includes at least one loop detachably connected to the base, the loop unfolding when the base is broken and the analytical aid is moved from the unused state.

10. The analytical aid of claim 1, further comprising a bending device that applies the bending force to the base to break the base.

11. An analytical aid for analyzing a body fluid, comprising:
a base that is breakable during use into a first segment and a second segment;
a lancet connected to the base;
a test element attached to the base;
a measuring head configured to analyze an application area of the test element; and
the analytical aid being movable from an unused position to a use position, wherein:
in the unused position a point of the lancet is covered; and
during movement from the unused position to the use position the base is broken into the first and second segments and one of the segments moves relative to the other, the lancet point becomes exposed for puncturing a body part, and the test element is moved to a position in which the test element is stretched over the measuring head.

12. The analytical aid of claim 11, further comprising a cover that covers the lancet point when the analytical aid is positioned in the unused position, wherein the lancet point punctures the cover when the analytical aid is moved from the unused position to the use position.

13. The analytical aid of claim 12, wherein at least one of the base and the cover comprises a material made brittle by irradiation.

14. The analytical aid of claim 11, wherein the base comprises a recess in which at least a portion of the lancet is positioned when the analytical aid is in the unused position.

15. The analytical aid of claim 11, wherein, during movement of the analytical aid from the unused position to the use position, the first segment pivots relative to the second segment.

16. The analytical aid of claim 11, wherein, in the unused position the test element defines a loop, the loop unfolding during movement of the analytical aid from the unused position to the use position.

17. The analytical aid of claim 11, wherein in the unused position the application area of the test element faces the base and in the use position the application area is stretched over and faces away from the measuring head.

18. The analytical aid of claim 11, wherein the base comprises a predetermined breaking position which defines the first and second segments.

19. The analytical aid of claim 18, wherein a first portion of the test element is attached to the first segment and a second portion of the test element is attached to the second segment, the test element having a flexible portion between the first portion and second portion that is stretched over the measuring head when the analytical aid is moved to the use position.

20. An analytical aid for analyzing a body fluid, comprising:
a base that is breakable about a brittle breaking point into a first segment and a second segment when stress is applied to the base, the base having a recess;
a lancet connected to the base and having a lancet point that is located in the recess when the analytical aid is in an unused state, the lancet point becoming exposed for puncturing a body part when the base is broken into the first segment and the second segment;
a test element at which a body fluid is analyzed attached to the base; and
a cover that covers the lancet point when the analytical aid is in the unused state, wherein the lancet ruptures the cover when the base is broken and the analytical aid is moved from the unused state.

21. The analytical aid of claim 20, wherein the recess includes a slit running substantially along a longitudinal direction of the analytical aid.

22. The analytical aid of claim 20, wherein the lancet comprises a first portion that is connected to the base and a second portion that includes the lancet point, the first and second portions being angled relative to one another.

23. The analytical aid of claim 20, wherein at least one of the base and the cover comprises a material made brittle by irradiation.

24. The analytical aid of claim 20, wherein the lancet point ruptures the cover when the base is broken and the analytical aid is moved from the unused state.

25. The analytical aid of claim 20, wherein the base comprises a predetermined breaking position comprising at least one of a notch and a channel formed in the base.

26. The analytical aid of claim 20, wherein the test element includes an application area for applying a sample to be analyzed, the application area facing the base when the analytical aid is in the unused state.

27. The analytical aid of claim 20, further comprising a measuring head, wherein the test element is at least partially flexible and is stretchable over the measuring head during use of the analytical aid.

28. The analytical aid of claim 27, wherein the test element includes at least one loop detachably connected to the base, the loop unfolding when the base is broken and the analytical aid is moved from the unused state.

29. The analytical aid of claim 20, further comprising a bending device that applies a bending force to the base to break the base.

* * * * *